United States Patent [19]

Fremont

[11] Patent Number: 4,727,166

[45] Date of Patent: Feb. 23, 1988

[54] AGGLOMERATES OF MALACHITE AND METHOD FOR THEIR PREPARATION

[75] Inventor: Joseph M. Fremont, Glen Mills, Pa.

[73] Assignee: E. I. du Pont de Nemours and Company, Wilmington, Del.

[21] Appl. No.: 930,059

[22] Filed: Nov. 12, 1986

Related U.S. Application Data

[60] Continuation of Ser. No. 712,226, Mar. 15, 1985, abandoned, which is a division of Ser. No. 617,072, Jun. 4, 1984, Pat. No. 4,536,491.

[51] Int. Cl.$^4$ .............................................. C07F 1/08
[52] U.S. Cl. .................................................... 556/112
[58] Field of Search ......................................... 556/112

[56] References Cited

U.S. PATENT DOCUMENTS

| | | | |
|---|---|---|---|
| 2,370,809 | 3/1945 | Morrell et al. | 556/112 |
| 2,440,612 | 4/1948 | Lichtenwalter | 556/112 |
| 3,149,149 | 9/1964 | Gorman et al. | 556/112 |
| 3,420,862 | 1/1969 | Long | 556/112 |
| 4,110,249 | 8/1978 | Fremont | 252/431 R |

*Primary Examiner*—Helen M. S. Sneed
*Attorney, Agent, or Firm*—David J. Gould

[57] ABSTRACT

Agglomerates of spheroidal masses of malachite crystals are prepared so that they contain silicic acid. These agglomerates can be used to prepare a copper-acetylide complex, which in turn can be used as a catalyst for the preparation of 1,4-butynediol from acetylene and formaldehyde.

4 Claims, No Drawings

AGGLOMERATES OF MALACHITE AND METHOD FOR THEIR PREPARATION

This application is a continuation of application Ser. No. 712,226 filed Mar. 15, 1985, now abandoned, which is a division of Ser. No. 617,072 filed June 4, 1984, now U.S. Pat. No. 4,536,491.

TECHNICAL FIELD

This invention relates to a new form of basic copper carbonate (malachite). It is more particularly directed to agglomerates of spheroidal masses of malachite crystals, to a method for preparing them, to copper acetylide catalysts prepared from the crystals, and to the use of the catalysts in the preparation of 1,4-butynediol from acetylene and formaldehyde.

BACKGROUND AND SUMMARY OF THE INVENTION

Large amounts of 1,4-butynediol are produced every year, chiefly as an intermediate in the preparation of tetrahydrofuran. In that preparation, the butynediol is hydrogenated to 1,4-butanediol, which is then dehydrated and cyclized to tetrahydrofuran.

It has been a common practice in years past to make 1,4-butynediol from acetylene and formaldehyde, using as a catalyst a copper acetylide complex. This is shown in my U.S. Pat. No. 4,110,249, in which I describe a catalyst made from malachite in the form of spheroidal masses of crystals which contain bismuth oxy-compounds to supress cuprene formation.

Such a catalyst is quite satisfactory, but I have found that its resistance to degradation by attrition can be improved if the malachite from which it is prepared also contains 0.5–3.5% by weight, of silicic acid. I have also found that the silicic acid gives the catalyst higher activity, and that this higher activity is sustained for a longer period than with my earlier catalyst.

DETAILED DESCRIPTION OF THE INVENTION

The malachite of the invention can be made by a three-stage process. In the first stage, an amorphous gel-like hydrated copper carbonate is prepared by bringing together, with agitation, in aqueous solution, a cupric salt, a bismuth salt, an alkali metal carbonate or bicarbonate, and silicic acid. In this first stage, only 30–60%, by volume, of the total amount of the cupric salt, the bismuth salt and the silicic acid needed are used, as precalculated before the preparative proces is begun.

Although any form of silicic acid can be used, I have found that a much more effective catalyst is obtained if the silicic acid is preformed by mixing together about 100 parts by volume of water, about 10 parts by weight of sodium silicate and about 10 parts by volume of nitric acid, with stirring. This gives a colloidal suspension of silicic acid, which can be used directly in preparing the malachite.

Any water soluble cupric salt can be used. Illustrative are the nitrate, the chloride and the sulfate. Cupric nitrate is preferred.

Similarly, any water soluble bismuth salt can be used. Illustrative are the nitrate, the oxycarbonate, the citrate, the sulfate and the phosphate. The nitrate is preferred.

Of the alkali metal carbonates and bicarbonates which can be used, sodium carbonate and sodium bicarbonate are preferred.

Each salt solution is prepared so that it contains as much salt as possible without it crystallizing from solution on standing or during use.

The copper salt solution, the bismuth salt solution and the silicic acid solution are then brought together in such proportions that the resulting mixture contains 1–10%, by weight of its copper content of bismuth salt, and 0.1–2% by weight of silicic acid. The pH of the mixture is maintained at about 5.5–7.5, preferably 6.5–7.0, by the addition of appropriate amounts of the alkali metal carbonate or bicarbonate solution.

The solutions can be brought together in any order, generally over a period of 10–30 minutes, with stirring. In a preferred embodiment, a solution of the copper salt, the bismuth salt and the silicic acid is prepared and this is fed to a small amount of water, simultaneously with a solution of the alkali metal carbonate or bicarbonate.

The resulting mixture of salts is held at a temperature of just slightly above the freezing point of the mixture to about 55° C., preferably 45°–55° C., with stirring. An amorphous mass of gel-like hydrated copper carbonate forms immediately.

In the second stage, the product of the first stage is held at a temperature of 45°–55° C., without stirring or agitation of any kind. Carbon dioxide evolves and masses of malachite crystals form. Crystal formation is ordinarily complete in 10–30 minutes.

In the third stage, this medium containing masses of malachite crystals is stirred and held at a temperature of 45°–55° C. while the remainders of the solutions of cupric salt, bismuth salt and silicic acid to be used are added, at about the same rate as that used in the first stage. As in the first stage, the pH of the reaction mass is maintained in the range 5.5–7.5, preferably 6.5–7.0, by addition of the alkali metal carbonate or bicarbonate solution. It is in this stage that the spheroidal masses of malachite crystals agglomerate to form the malachite of the invention.

After this third stage is complete, ordinarily a matter of 10–60 minutes, the malachite is filtered from the reaction medium and washed free of residual salts with water.

The resulting product, agglomerates of spheroidal masses of malachite crystals, contains 0.5–3.5% by weight (calculated as $SiO_2$) of silicic acid, preferably 0.5–1%. This is uniformly distributed throughout the crystals, although with higher concentrations, a bit more tends to appear at the surfaces of the crystals.

The crystals also contain 1–7%, by weight, of uniformly distributed bismuth oxy-compound.

Although the benefits of my invention are largely independent of the dimensions of the spheroidal masses of malachite crystals and the agglomerates of these masses, I have found that a catalyst much easier to filter from the reaction mass and of a much more uniform composition can be obtained if the malachite from which it is prepared is composed of agglomerates having an average longest dimension of about 15 microns, with at least about 95% having a longest dimension of about 14–18 microns, and if the spheroidal masses of crystals have an average longest dimension of about 5 microns, with at least about 95% of the masses having a longest dimension of 3–8 microns, all as determined by a Coulter Counter, or as measured optically against a standard.

This preferred malachite can be prepared according to the method just described if, in the first stage, the solutions are brought together in a small amount of water containing a small amount, e.g., about 0.2–2%, by weight, of a pre-formed seed of the malachite of the invention. This seed can be added directly to the water, or it can be present as residue from a previous preparation.

The malachite produced in this way can be converted to a copper-acetylide complex by preparing a slurry of it in water and then subjecting this slurry to the action of acetylene and formaldehyde. This procedure is described in more detail in Kirchner U.S. Pat. No. 3,650,985, beginning in column 5. The portion of the Kirchner patent which describes this procedure is incorporated into this specificaton by reference.

This copper-acetylide complex can be used directly as a catalyst for the reaction of acetylene and formaldehyde to produce 1,4-butynediol. The complex is used in the customary way and in the usual amounts, and no special techniques or precautions are needed. Details for this use can be found in the aforementioned Kirchner patent.

EXAMPLES

Those skilled in this art will be able to practice this invention more easily after referring to the following illustrative examples.

These artisans will no doubt be able to compose numerous variations on the themes disclosed, such as changing the amounts of components used slightly but insignificantly from those shown, adding innocuous substances, or substituting equivalent or nearly equivalent components for those shown. I consider all these variations to be part of my inventive concept.

In the examples, all parts are by weight.

EXAMPLE 1

Preparation of Malachite (a) In 900 parts of water were dissolved
  $Cu(NO_3)_2 \cdot H_2O$: 980 parts
  $Bi(NO_3)_3 \cdot 5H_2O$: 35 parts
  $HNO_3$ (concentrated): 90 parts
(b) A mixture was prepared of
  Water: 100 parts
  $HNO_3$ (concentrated): 10 parts
  Sodium silicate: 10 parts
(c) The mixture of (b) was added to the solution of (a), with stirring.
(d) 675 parts of anhydrous $Na_2CO_3$ were dissolved in 3300 parts of water.
(e) A reaction vessel was charged with 3300 parts of water containing 0.2 parts of malachite crystals prepared in a previous run.

This charge was heated to and held at 45° C., with stirring, while half of the solution of (c) was fed in over a 15 minute period. Enough of the solution of (d) was concurrently fed into the charge to hold the pH at 6.5–7.0.

When the feed was complete, stirring was stopped and the temperature of the reaction mass held at 45° C. for 20 minutes. A blue-green gel formed which gradually changed to masses of green malachite crystals.

Stirring was then resumed, and the remainder of solution (c) was added to the reaction mass over a 15 minute period, while the temperature of the mass was held at about 47° C. and the pH held at 6.5–7.0 with solution (d).

The agglomerates which formed had an average diameter of 15–17 microns, and were composed of spherical masses of malachite crystals, the masses having an average diameter of about 6 microns. The crystals contained 0.67%, by weight, of silicic acid.

These agglomerates were filtered from the solution, washed with water, and dried.

EXAMPLE 2

Preparation of Copper-acetylide Complex

A reaction vessel was charged with 600 parts of a 47% solution of formaldehyde in water (having a pH of 7.0), and 100 parts of the malachite prepared in Example 1.

An acetylene nitrogen mixture was sparged into the vessel at a rate which kept the solids in suspension and gave a pressure of 5 psig. The temperature of the reaction mass was held at 65°–75° C. and its pH was held at 5.0–6.5 with saturated sodium carbonate solution.

The effluent gas stream, composed of carbon dioxide, nitrogen and acetylene, was bifurcated. One portion was vented to the atmosphere and the other recycled to the reactor. The vent rate and acetylene feed rate into the reactor were controlled to keep the acetylene concentration in the reactor in the range 1–5% at all times.

After about 6 hours, $CO_2$ evolution declined. The vent rate and the acetylene feed were then increased so that acetylene replaced the vented $CO_2$, until $CO_2$ evolution stopped.

Pressure was then released, the product cooled and removed from the reactor.

EXAMPLE 3

Preparation of 1,4-butynediol

A reaction vessel was charged with the catalyst prepared in Example 2 and 600 parts of formaldehyde (45% solution in water). A stream of acetylene was then continuously passed through the vessel at a rate which kept the solids suspended and provided an acetylene pressure of about 5 psig. The temperature of the reaction mass was held at about 90° C., and its pH at about 6 with a saturated solution of sodium bicarbonate.

The reaction was continued for two hours, at which point about 5%, by weight, of the original formaldehyde charge remained.

I claim:

1. A process for the formation of a copper-acetylide complex, the process comprising subjecting agglomerates of spheroidal masses of malachite crystals, which crystals contain 1–7%, by weight, of bismuth oxycarbonate and 0.5–3.5%, by weight (calculated as $SiO_2$) of silicic acid, to the action of acetylene and formaldehyde.

2. A process for the formation of a copper-acetylide complex, the process comprising subjecting agglomerates like those described in claim 1, having an average longest dimension of about 15 microns, with at least about 95% of the agglomerates having a longest dimension of 14–18 microns, and the spheroidal masses of malachite crystals having an average longest dimension of about 5 microns, with at least about 95% of the masses having a longest dimension of 3–8 microns, to the action of formaldehyde and acetylene.

3. The copper acetylide complex produced by the process of claim 1.

4. The copper acetylide complex produced by the process of claim 2.

* * * * *